(12) United States Patent
Hannula et al.

(10) Patent No.: US 7,810,359 B2
(45) Date of Patent: Oct. 12, 2010

(54) HEADBAND WITH TENSION INDICATOR

(75) Inventors: Don Hannula, San Luis Obispo, CA (US); Joseph Coakley, Dublin, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1622 days.

(21) Appl. No.: 10/677,742

(22) Filed: Oct. 1, 2003

(65) Prior Publication Data

US 2004/0117891 A1    Jun. 24, 2004

Related U.S. Application Data

(60) Provisional application No. 60/415,468, filed on Oct. 1, 2002.

(51) Int. Cl.
*D04B 1/24*    (2006.01)
(52) U.S. Cl. .......................................... 66/172 E; 2/181
(58) Field of Classification Search .............. 66/169 R, 66/170, 171, 172 E; 2/171, 181, 181.2
See application file for complete search history.

(56) References Cited

U.S. PATENT DOCUMENTS

| | | | |
|---|---|---|---|
| 4,025,733 A | 5/1977 | Klar et al. | |
| 4,047,400 A * | 9/1977 | Thorneburg | 66/171 |
| 4,321,930 A | 3/1982 | Jobsis et al. | |
| 4,462,116 A | 7/1984 | Sanzone et al. | |
| 4,499,741 A * | 2/1985 | Harris | 66/171 |
| 4,510,938 A | 4/1985 | Jobsis et al. | |
| 4,570,638 A | 2/1986 | Stoddart et al. | |
| 4,675,919 A | 6/1987 | Heine et al. | |
| 4,739,757 A | 4/1988 | Edwards | |
| 4,775,116 A | 10/1988 | Klein | |
| 4,784,162 A | 11/1988 | Ricks et al. | |
| 4,802,485 A | 2/1989 | Bowers et al. | |
| 4,825,872 A | 5/1989 | Tan et al. | |

(Continued)

FOREIGN PATENT DOCUMENTS

CN    1306260    8/2001

(Continued)

OTHER PUBLICATIONS

Yamaya et al., "Validity of Pulse Oximetry During Maximal Exercise in Normoxia, Hypoxia, and Hyperoxia"; Journal of Applied Physiology (2002), vol. 92, Issue 1, pp. 162-168.

(Continued)

*Primary Examiner*—Danny Worrell
(74) *Attorney, Agent, or Firm*—Fletcher Yoder

(57) ABSTRACT

A headband with a tension indicator having an elastic segment sized to fit around a wearer's head; and a non-elastic segment being smaller than and attached with the elastic segment. The non-elastic segment is sized to span a portion of the elastic segment when the elastic segment is stretched, and the non-elastic segment is larger than the portion of the elastic segment it spans when the elastic segment is not stretched. The non-elastic segment is attached with the elastic segment in such a manner that the non-elastic segment projects out from the surface of the elastic portion when the headband is not sufficiently tight, thus creating a loop which provides a visual indication that the headband needs re-tightening.

23 Claims, 4 Drawing Sheets

U.S. PATENT DOCUMENTS

| | | | |
|---|---|---|---|
| 4,825,879 A | 5/1989 | Tan et al. | |
| 4,833,734 A * | 5/1989 | Der Estephanian | 2/171 |
| 4,838,279 A | 6/1989 | Fore | |
| 4,856,116 A | 8/1989 | Sullivan | |
| 4,890,619 A | 1/1990 | Hatschek | |
| 4,910,804 A * | 3/1990 | Lidgren | 2/209.3 |
| 4,911,167 A | 3/1990 | Corenman et al. | |
| 4,918,758 A * | 4/1990 | Rendina | 2/171 |
| 4,930,888 A | 6/1990 | Freisleben et al. | |
| 4,942,877 A | 7/1990 | Sakai et al. | |
| 4,972,331 A | 11/1990 | Chance | |
| 4,977,011 A | 12/1990 | Smith | |
| 4,991,234 A | 2/1991 | Greenberg | |
| 4,996,975 A | 3/1991 | Nakamura | |
| 5,005,374 A | 4/1991 | Spitler et al. | |
| 5,054,488 A | 10/1991 | Muz | |
| 5,080,096 A | 1/1992 | Hooper et al. | |
| 5,080,098 A | 1/1992 | Willett et al. | |
| H1039 H | 4/1992 | Tripp, Jr. et al. | |
| 5,111,817 A | 5/1992 | Clark et al. | |
| 5,119,815 A | 6/1992 | Chance | |
| 5,122,974 A | 6/1992 | Chance | |
| 5,125,403 A | 6/1992 | Culp | |
| 5,167,230 A | 12/1992 | Chance | |
| 5,188,108 A | 2/1993 | Secker | |
| 5,191,891 A | 3/1993 | Righter | |
| 5,209,230 A | 5/1993 | Swedlow et al. | |
| 5,214,409 A | 5/1993 | Beigel | |
| 5,217,012 A | 6/1993 | Young et al. | |
| 5,217,013 A | 6/1993 | Lewis et al. | |
| 5,241,300 A | 8/1993 | Buschmann | |
| 5,246,003 A | 9/1993 | DeLonzor | |
| 5,253,645 A | 10/1993 | Friedman et al. | |
| 5,267,563 A | 12/1993 | Swedlow et al. | |
| 5,267,567 A | 12/1993 | Aung et al. | |
| 5,295,490 A | 3/1994 | Dodakian | |
| 5,313,940 A | 5/1994 | Fuse et al. | |
| 5,337,744 A | 8/1994 | Brianigan | |
| 5,348,008 A | 9/1994 | Bornn et al. | |
| 5,353,798 A | 10/1994 | Sieben | |
| 5,354,979 A | 10/1994 | Adelson et al. | |
| 5,357,953 A | 10/1994 | Merrick et al. | |
| 5,368,025 A | 11/1994 | Young et al. | |
| 5,368,562 A | 11/1994 | Blomquist et al. | |
| 5,383,874 A | 1/1995 | Jackson et al. | |
| 5,392,777 A | 2/1995 | Swedlow et al. | |
| 5,398,689 A | 3/1995 | Connor et al. | |
| 5,400,267 A | 3/1995 | Denen et al. | |
| 5,405,269 A | 4/1995 | Stupecky | |
| 5,405,614 A | 4/1995 | D'Angelo et al. | |
| 5,413,099 A | 5/1995 | Schmidt et al. | |
| 5,413,101 A | 5/1995 | Sugiura | |
| 5,413,102 A | 5/1995 | Schmidt et al. | |
| 5,415,166 A | 5/1995 | Imran | |
| 5,425,360 A | 6/1995 | Nelson | |
| 5,431,170 A | 7/1995 | Mathews | |
| 5,437,275 A | 8/1995 | Amundsen et al. | |
| 5,437,634 A | 8/1995 | Amano | |
| 5,444,254 A | 8/1995 | Thomson | |
| 5,451,763 A | 9/1995 | Pickett et al. | |
| 5,452,717 A | 9/1995 | Brianigan et al. | |
| 5,465,714 A | 11/1995 | Scheuing | |
| 5,469,845 A | 11/1995 | DeLonzor et al. | |
| 5,482,034 A | 1/1996 | Lewis et al. | |
| 5,490,523 A | 2/1996 | Isaacson et al. | |
| 5,528,519 A | 6/1996 | Ohkura et al. | |
| 5,546,955 A | 8/1996 | Wilk | |
| 5,551,423 A | 9/1996 | Sugiura | |
| 5,562,718 A | 10/1996 | Palermo | |
| 5,564,108 A | 10/1996 | Hunsaker et al. | |
| 5,564,417 A | 10/1996 | Chance | |
| 5,584,296 A | 12/1996 | Cui et al. | |
| 5,592,408 A | 1/1997 | Keskin et al. | |
| 5,596,987 A | 1/1997 | Chance | |
| 5,617,865 A | 4/1997 | Palczewska et al. | |
| 5,617,866 A | 4/1997 | Marian, Jr. | |
| 5,627,323 A | 5/1997 | Stern | |
| 5,634,466 A | 6/1997 | Gruner | |
| 5,638,593 A | 6/1997 | Gerhardt et al. | |
| 5,638,818 A | 6/1997 | Diab et al. | |
| 5,640,953 A | 6/1997 | Bishop et al. | |
| 5,645,059 A | 7/1997 | Fine et al. | |
| 5,645,440 A | 7/1997 | Tobler et al. | |
| 5,645,586 A | 7/1997 | Meltzer | |
| 5,646,416 A | 7/1997 | Van De Velde | |
| 5,671,750 A | 9/1997 | Shinoda | |
| 5,673,708 A | 10/1997 | Athanasiou et al. | |
| 5,678,544 A | 10/1997 | DeLonzor et al. | |
| 5,681,285 A | 10/1997 | Ford et al. | |
| 5,683,434 A | 11/1997 | Archer | |
| 5,697,363 A | 12/1997 | Hart | |
| 5,697,367 A | 12/1997 | Lewis et al. | |
| 5,701,894 A | 12/1997 | Cherry et al. | |
| 5,706,820 A | 1/1998 | Hossack et al. | |
| 5,732,475 A | 3/1998 | Sacks et al. | |
| 5,738,612 A | 4/1998 | Tsuda | |
| 5,743,856 A | 4/1998 | Oka et al. | |
| 5,743,857 A | 4/1998 | Shinoda et al. | |
| 5,752,913 A | 5/1998 | Oka | |
| 5,752,920 A | 5/1998 | Ogura et al. | |
| 5,758,644 A | 6/1998 | Diab et al. | |
| 5,772,601 A | 6/1998 | Oka et al. | |
| 5,776,058 A | 7/1998 | Levinson et al. | |
| 5,776,071 A | 7/1998 | Inuaki et al. | |
| 5,779,631 A | 7/1998 | Chance | |
| 5,779,639 A | 7/1998 | Yeung | |
| 5,782,757 A | 7/1998 | Diab et al. | |
| 5,786,592 A | 7/1998 | Hök | |
| 5,791,347 A | 8/1998 | Flaherty et al. | |
| 5,791,348 A | 8/1998 | Aung et al. | |
| 5,792,052 A | 8/1998 | Isaacson et al. | |
| 5,792,058 A | 8/1998 | Young et al. | |
| 5,797,841 A | 8/1998 | Delonzor et al. | |
| 5,810,724 A | 9/1998 | Gronvall | |
| 5,813,980 A | 9/1998 | Levinson et al. | |
| 5,823,012 A * | 10/1998 | Hacskaylo | 66/171 |
| 5,823,952 A | 10/1998 | Levinson et al. | |
| 5,826,277 A | 10/1998 | McConville | |
| 5,830,136 A | 11/1998 | Delonzor et al. | |
| 5,830,137 A | 11/1998 | Scharf | |
| 5,830,148 A | 11/1998 | Inuaki et al. | |
| 5,830,149 A | 11/1998 | Oka et al. | |
| 5,833,602 A | 11/1998 | Osemwota | |
| 5,836,887 A | 11/1998 | Oka et al. | |
| 5,839,439 A | 11/1998 | Nierlich et al. | |
| RE36,000 E | 12/1998 | Swedlow et al. | |
| 5,842,981 A | 12/1998 | Larsen et al. | |
| 5,842,982 A | 12/1998 | Mannheimer | |
| 5,851,179 A | 12/1998 | Ritson et al. | |
| 5,853,364 A | 12/1998 | Baker, Jr. et al. | |
| 5,857,974 A | 1/1999 | Eberle et al. | |
| 5,860,932 A | 1/1999 | Goto et al. | |
| 5,860,957 A | 1/1999 | Jacobsen et al. | |
| 5,868,133 A | 2/1999 | DeVries et al. | |
| 5,870,626 A | 2/1999 | Lebeau | |
| 5,872,713 A | 2/1999 | Douglas et al. | |
| 5,873,821 A | 2/1999 | Chance et al. | |
| 5,879,294 A | 3/1999 | Anderson et al. | |
| 5,891,021 A | 4/1999 | Dillon et al. | |
| 5,891,026 A | 4/1999 | Wang et al. | |
| 5,895,359 A | 4/1999 | Peel | |
| 5,902,235 A | 5/1999 | Lewis et al. | |
| 5,906,581 A | 5/1999 | Tsuda | |
| 5,913,819 A | 6/1999 | Taylor et al. | |

| Patent | Date | Inventor |
|---|---|---|
| 5,916,154 A | 6/1999 | Hobbs et al. |
| 5,919,133 A | 7/1999 | Taylor et al. |
| 5,931,790 A | 8/1999 | Peel |
| 5,931,791 A | 8/1999 | Saltzstein et al. |
| 5,934,925 A | 8/1999 | Tobler et al. |
| 5,936,539 A | 8/1999 | Fuchs |
| 5,947,905 A | 9/1999 | Hadjicostis et al. |
| 5,954,053 A | 9/1999 | Chance et al. |
| 5,957,850 A | 9/1999 | Marian, Jr. et al. |
| 5,964,701 A | 10/1999 | Asada et al. |
| 5,980,464 A | 11/1999 | Tsuda |
| 5,983,129 A | 11/1999 | Cowan et al. |
| 5,987,343 A | 11/1999 | Kinast |
| 5,987,351 A | 11/1999 | Chance |
| 5,991,648 A | 11/1999 | Levin |
| 5,995,077 A | 11/1999 | Wilcox et al. |
| 5,995,855 A | 11/1999 | Kiani et al. |
| 5,995,856 A | 11/1999 | Mannheimer et al. |
| 5,995,857 A | 11/1999 | Toomim et al. |
| 6,007,492 A | 12/1999 | Goto et al. |
| 6,011,986 A | 1/2000 | Diab et al. |
| 6,022,320 A | 2/2000 | Ogura et al. |
| 6,027,453 A | 2/2000 | Miwa et al. |
| 6,030,351 A | 2/2000 | Schmidt et al. |
| 6,031,603 A | 2/2000 | Fine et al. |
| 6,036,651 A | 3/2000 | Inuaki et al. |
| 6,041,247 A | 3/2000 | Weckstrom et al. |
| 6,047,201 A | 4/2000 | Jackson |
| 6,047,203 A | 4/2000 | Sackner et al. |
| 6,049,958 A | 4/2000 | Eberle et al. |
| 6,050,951 A | 4/2000 | Friedman et al. |
| 6,052,619 A | 4/2000 | John |
| 6,073,038 A | 6/2000 | Wang et al. |
| 6,084,380 A | 7/2000 | Burton |
| 6,085,752 A | 7/2000 | Kehr et al. |
| 6,088,607 A | 7/2000 | Diab et al. |
| 6,106,780 A | 8/2000 | Douglas et al. |
| 6,112,107 A | 8/2000 | Hannula |
| 6,115,621 A | 9/2000 | Chin |
| 6,118,382 A | 9/2000 | Hibbs et al. |
| 6,134,459 A | 10/2000 | Roberts et al. |
| 6,144,867 A | 11/2000 | Walker et al. |
| 6,144,868 A | 11/2000 | Parker |
| 6,149,481 A | 11/2000 | Wang et al. |
| 6,152,754 A | 11/2000 | Gerhardt et al. |
| 6,154,667 A | 11/2000 | Miura et al. |
| 6,162,188 A | 12/2000 | Barnea |
| 6,165,173 A | 12/2000 | Kamdar et al. |
| 6,171,258 B1 | 1/2001 | Karakasoglu et al. |
| 6,173,196 B1 | 1/2001 | Delonzor et al. |
| 6,179,786 B1 | 1/2001 | Young |
| 6,181,959 B1 | 1/2001 | Schollermann et al. |
| 6,184,521 B1 | 2/2001 | Coffin, IV et al. |
| 6,186,953 B1 | 2/2001 | Narimatsu |
| 6,186,954 B1 | 2/2001 | Narimatsu |
| 6,190,325 B1 | 2/2001 | Narimatsu |
| 6,196,974 B1 | 3/2001 | Miwa |
| 6,198,952 B1 | 3/2001 | Miesel |
| 6,199,550 B1 | 3/2001 | Wiesmann et al. |
| 6,209,144 B1 | 4/2001 | Carter |
| 6,216,021 B1 | 4/2001 | Franceschini et al. |
| 6,223,063 B1 | 4/2001 | Chaiken et al. |
| 6,241,680 B1 | 6/2001 | Miwa |
| 6,248,083 B1 | 6/2001 | Smith et al. |
| 6,251,076 B1 | 6/2001 | Hovland et al. |
| 6,251,080 B1 | 6/2001 | Henkin et al. |
| 6,251,081 B1 | 6/2001 | Narimatsu |
| 6,251,113 B1 | 6/2001 | Appelbaum et al. |
| 6,256,523 B1 | 7/2001 | Diab et al. |
| 6,256,524 B1 | 7/2001 | Walker et al. |
| 6,263,221 B1 | 7/2001 | Chance et al. |
| 6,263,223 B1 | 7/2001 | Shepherd et al. |
| 6,280,213 B1 | 8/2001 | Tobler et al. |
| 6,282,450 B1 | 8/2001 | Hartlaub et al. |
| 6,283,922 B1 | 9/2001 | Goto et al. |
| 6,285,895 B1 | 9/2001 | Ristolainen et al. |
| 6,306,076 B1 | 10/2001 | Gill |
| 6,308,089 B1 | 10/2001 | von der Ruhr et al. |
| 6,321,100 B1 | 11/2001 | Parker |
| 6,322,516 B1 | 11/2001 | Masuda et al. |
| 6,343,223 B1 | 1/2002 | Chin et al. |
| 6,343,224 B1 | 1/2002 | Parker |
| 6,346,886 B1 | 2/2002 | De La Huerga |
| 6,349,228 B1 | 2/2002 | Kiani et al. |
| 6,356,774 B1 | 3/2002 | Bernstein et al. |
| 6,362,622 B1 | 3/2002 | Stauber et al. |
| 6,368,282 B1 | 4/2002 | Oka et al. |
| 6,370,411 B1 | 4/2002 | Osadchy et al. |
| 6,377,829 B1 | 4/2002 | Al-Ali |
| 6,381,480 B1 | 4/2002 | Kuroyama |
| 6,381,481 B1 | 4/2002 | Levendowski et al. |
| 6,385,486 B1 | 5/2002 | John et al. |
| 6,385,821 B1 | 5/2002 | Modgil et al. |
| 6,387,092 B1 | 5/2002 | Burnside et al. |
| 6,388,240 B2 | 5/2002 | Schulz et al. |
| 6,397,091 B2 | 5/2002 | Diab et al. |
| 6,405,075 B1 | 6/2002 | Levin |
| 6,416,471 B1 | 7/2002 | Kumar et al. |
| 6,416,474 B1 | 7/2002 | Penner et al. |
| 6,417,774 B1 | 7/2002 | Hibbs et al. |
| 6,423,010 B1 | 7/2002 | Friedman et al. |
| 6,430,423 B2 | 8/2002 | DeLonzor et al. |
| 6,432,050 B1 | 8/2002 | Porat et al. |
| 6,450,168 B1 | 9/2002 | Nguyen |
| 6,450,957 B1 | 9/2002 | Yoshimi et al. |
| 6,450,981 B1 | 9/2002 | Shabty et al. |
| 6,454,708 B1 | 9/2002 | Ferguson et al. |
| 6,615,065 B1 | 9/2003 | Barrett et al. |
| 6,748,254 B2 | 6/2004 | O'Neil et al. |
| 6,811,538 B2 | 11/2004 | Westbrook et al. |
| 6,934,570 B2 | 8/2005 | Kiani et al. |
| 6,934,571 B2 | 8/2005 | Wiesmann et al. |
| 6,985,763 B2 | 1/2006 | Boas et al. |
| 7,001,334 B2 | 2/2006 | Reed et al. |
| 7,027,850 B2 | 4/2006 | Wasserman et al. |
| 7,047,054 B2 | 5/2006 | Benni |
| 7,047,055 B2 | 5/2006 | Boas et al. |
| 7,054,453 B2 | 5/2006 | Boas et al. |
| 7,054,454 B2 | 5/2006 | Boas et al. |
| 7,072,704 B2 | 7/2006 | Bucholz |
| 7,085,597 B2 | 8/2006 | Fein et al. |
| 7,113,815 B2 | 9/2006 | O'Neil et al. |
| 7,132,641 B2 | 11/2006 | Schulz et al. |
| 7,171,251 B2 | 1/2007 | Sarussi et al. |
| 7,181,264 B2 | 2/2007 | Wiesmann et al. |
| 7,204,250 B1 | 4/2007 | Burton |
| 7,220,220 B2 | 5/2007 | Stubbs et al. |
| 7,245,953 B1 | 7/2007 | Parker |
| 7,248,910 B2 | 7/2007 | Li et al. |
| 7,297,119 B2 | 11/2007 | Westbrook et al. |
| 7,313,427 B2 | 12/2007 | Benni |
| 7,349,726 B2 | 3/2008 | Casciani et al. |
| 7,376,454 B2 | 5/2008 | Casciani et al. |
| 7,415,298 B2 | 8/2008 | Casciani et al. |
| 2001/0000790 A1 | 5/2001 | Delonzor et al. |
| 2001/0009398 A1 | 7/2001 | Sekura et al. |
| 2002/0013538 A1 | 1/2002 | Teller |
| 2002/0042558 A1 | 4/2002 | Mendelson |
| 2002/0052539 A1 | 5/2002 | Haller et al. |
| 2002/0084904 A1 | 7/2002 | De La Huerga |
| 2002/0091335 A1 | 7/2002 | John et al. |
| 2002/0095092 A1 | 7/2002 | Kondo et al. |
| 2002/0103445 A1 | 8/2002 | Rahdert et al. |
| 2002/0109600 A1 | 8/2002 | Mault et al. |
| 2002/0124295 A1 | 9/2002 | Fenwick et al. |
| 2003/0109775 A1 | 6/2003 | O'Neil et al. |

| | | | | | | |
|---|---|---|---|---|---|---|
| 2003/0225323 | A1 | 12/2003 | Kiani et al. | FR | 2555744 | 11/1983 |
| 2003/0236452 | A1 | 12/2003 | Melker et al. | FR | 2601137 | 1/1988 |
| 2004/0163648 | A1 | 8/2004 | Burton | GB | 834469 | 5/1960 |
| 2004/0221370 | A1 | 11/2004 | Hannula et al. | GB | 2135074 | 8/1984 |
| 2005/0027207 | A1 | 2/2005 | Westbrook et al. | JP | 55024614 | 2/1980 |
| 2005/0113656 | A1 | 5/2005 | Chance | JP | 04057161 | 2/1992 |
| 2005/0277819 | A1 | 12/2005 | Kiani et al. | JP | 07336597 | 12/1995 |
| 2006/0195026 | A1 | 8/2006 | Casciani et al. | JP | 08111295 | 4/1996 |
| 2006/0195027 | A1 | 8/2006 | Casciani et al. | JP | 08112257 | 5/1996 |
| 2006/0211929 | A1 | 9/2006 | Casciani et al. | JP | 08336546 | 12/1996 |
| 2006/0217604 | A1 | 9/2006 | Fein et al. | JP | 09010319 | 1/1997 |
| 2006/0217605 | A1 | 9/2006 | Fein et al. | JP | 09154937 | 6/1997 |
| 2006/0217606 | A1 | 9/2006 | Fein et al. | JP | 10314149 | 12/1998 |
| 2006/0217607 | A1 | 9/2006 | Fein et al. | JP | 11259583 | 9/1999 |
| 2006/0217608 | A1 | 9/2006 | Fein et al. | JP | 2000/189440 | 7/2000 |
| 2006/0229510 | A1 | 10/2006 | Fein et al. | JP | 2001/161648 | 6/2001 |
| 2006/0229511 | A1 | 10/2006 | Fein et al. | JP | 2001/190498 | 7/2001 |
| 2006/0276700 | A1 | 12/2006 | O'Neil et al. | JP | 2001/308576 | 11/2001 |
| 2007/0149871 | A1 | 6/2007 | Sarussi et al. | JP | 2001/332832 | 11/2001 |
| 2007/0293746 | A1 | 12/2007 | Sarussi et al. | JP | 2001/346775 | 12/2001 |
| 2008/0009691 | A1 | 1/2008 | Parker et al. | JP | 2002/065647 | 3/2002 |
| 2008/0076988 | A1 | 3/2008 | Sarussi et al. | RU | 2132204 | 6/1999 |
| 2008/0076990 | A1 | 3/2008 | Sarussi et al. | WO | WO9001293 | 2/1990 |

FOREIGN PATENT DOCUMENTS

| | | |
|---|---|---|
| DE | 3705493 | 8/1988 |
| DE | 3744781 | 1/1989 |
| DE | 3810411 | 10/1989 |
| DE | 3927038 | 2/1991 |
| DE | 4429845 | 10/1995 |
| DE | 29515877 U1 | 11/1995 |
| DE | 19541605 | 5/1997 |
| DE | 19939302 | 5/2001 |
| DE | 10029205 | 1/2002 |
| EP | 268850 | 6/1988 |
| EP | 0313238 | 4/1989 |
| EP | 338518 | 10/1989 |
| EP | 463620 | 1/1992 |
| EP | 543172 | 5/1993 |
| EP | 0572684 | 12/1993 |
| EP | 0573137 | 12/1993 |
| EP | 578530 | 1/1994 |
| EP | 580385 | 1/1994 |
| EP | 775311 | 8/1994 |
| EP | 621026 | 10/1994 |
| EP | 0631756 | 1/1995 |
| EP | 0631756 A1 | 1/1995 |
| EP | 665025 | 8/1995 |
| EP | 0695139 | 2/1996 |
| EP | 0721110 | 7/1996 |
| EP | 1048323 | 2/2000 |
| EP | 996063 | 4/2000 |
| EP | 1130412 | 5/2001 |
| EP | 1169965 | 1/2002 |
| WO | WO9111137 | 8/1991 |
| WO | WO 9115151 | 10/1991 |
| WO | WO 9118550 | 12/1991 |
| WO | WO 9220273 | 11/1992 |
| WO | WO 95/06430 | 3/1995 |
| WO | WO9512349 | 5/1995 |
| WO | WO 9615714 | 5/1996 |
| WO | WO 9616591 | 6/1996 |
| WO | WO 9641138 | 12/1996 |
| WO | WO 9720494 | 6/1997 |
| WO | WO 9720497 | 6/1997 |
| WO | WO9817174 | 4/1998 |
| WO | WO9947039 | 9/1999 |
| WO | WO 9963883 | 12/1999 |
| WO | WO0059374 | 10/2000 |
| WO | WO 00/78209 | 12/2000 |
| WO | WO 01/01855 | 1/2001 |
| WO | WO 01/17425 | 3/2001 |
| WO | WO0176471 | 10/2001 |
| WO | WO 01/87224 | 11/2001 |
| WO | WO 02/15784 | 2/2002 |
| WO | WO 02/65901 | 8/2002 |
| WO | WO 02/066977 | 8/2002 |
| WO | WO03071928 | 9/2003 |

OTHER PUBLICATIONS

Bebout et al., "Effects of Cold-Induced Peripheral Vasoconstriction on Pulse Amplitude at Various Pulse Oximeter Sensor Sites"; Published Abstract, Anesthesiology 2002; 96:A558.

\* cited by examiner

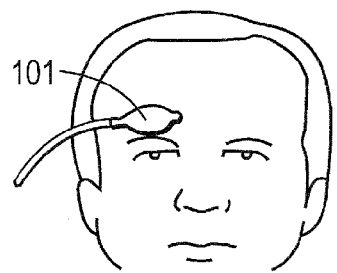
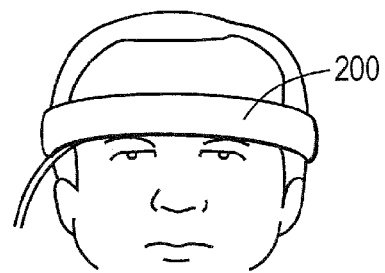
FIG.1　　　　　　　FIG.2
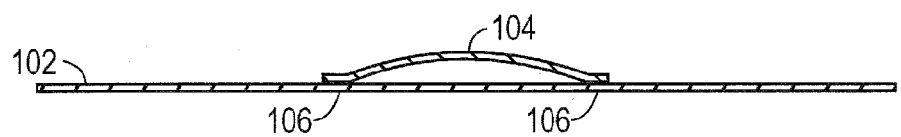
FIG.3

HEADBAND WITH TENSION INDICATOR

CROSS-REFERENCES TO RELATED APPLICATIONS

This application claims the benefit of U.S. Provisional Patent Application No. 60/415,468, filed Oct. 1, 2002, which application is incorporated herein by reference in its entirety for all purposes.

BACKGROUND OF THE INVENTION

The present invention relates to headbands, and in particular to headbands that have a tension indicator for indicating when a headband is appropriately stretched and is thus capable of imparting an appropriate level of pressure to a wearer's head.

Various headband devices are known. These include athletic type headband devices as well as more sophisticated headband devices, such as those used to mount devices carried on the head. Some headband devices are used to apply a certain level of pressure to the region under the headband. Such applied pressures are useful, for example, to support a medical sensor for the wearer of the headband. In such circumstances, there is a need for an improved headband having a tension indicator.

BRIEF SUMMARY OF THE INVENTION

Embodiments of the present invention are directed to a head band with a tension indicator. In one embodiment, the present invention provides a headband having an elastic segment sized to fit around a wearer's head; and a non-elastic segment being smaller than and attached with the elastic segment. The non-elastic segment is sized to span a portion of the elastic segment when the elastic segment is stretched, and the non-elastic segment is larger than the portion of the elastic segment it spans when the elastic segment is not stretched.

In one aspect, the non-elastic segment is attached with the elastic segment in such a manner that the non-elastic segment projects out from the surface of the elastic portion when the headband is not sufficiently tight, thus creating a loop which provides a visual indication that the headband needs re-tightening.

In another aspect, the non-elastic segment is formed with a fold or a crease, which causes the non-elastic portion to project out from the surface of the elastic portion in a pronounced fashion as the elastic segment retracts.

In another aspect, the non-elastic segment is sized to not project out from the surface of the elastic portion when the headband is sufficiently tight, thus indicating an adequate level of tension corresponding with delivering a pressure in the range higher than the venous pressure and lower than the capillary pressure to the forehead of the wearer.

In an alternate embodiment, the present invention provides a headband having an inelastic segment sized to fit around a wearer's head; and an elastic segment that is smaller than and attached with the inelastic segment. The elastic segment is sized to span a portion of the inelastic segment when the elastic segment is stretched, and the elastic segment is smaller than the portion of the inelastic segment it spans when the elastic segment is not stretched.

For a further understanding of the nature and advantages of the invention, reference should be made to the following description taken in conjunction with the accompanying drawings.

BRIEF DESCRIPTION OF THE DRAWINGS

FIG. 1 is a diagram of a forehead oximetry sensor being applied to a patient.

FIG. 2 is a diagram of a forehead oximetry sensor being held to a patient's forehead with a headband.

FIG. 3 is a diagram of one embodiment of the headband in accordance with the present invention.

DETAILED DESCRIPTION OF THE INVENTION

Figure 4A:
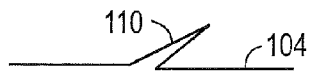
FIG. 4A is a top view detail diagram of the crease or fold of FIG. 4.

The embodiments of the present invention are directed towards a headband with a tension indicator. Such a headband may be used to support the administration of a health care related service to a patient. Such a service may include the placement of a sensor 101 on a patient's forehead, such as for example, an oximetry sensor (e.g., those manufactured by Nellcor Puritan Bennett, the assignee herein), as is shown in FIG. 1. A typical pulse oximeter measures two physiological parameters, percent oxygen saturation of arterial blood hemoglobin ($SpO_2$ or sat) and pulse rate. Oxygen saturation can be estimated using various techniques. In one common technique, the photocurrent generated by the photo-detector is conditioned and processed to determine the ratio of modulation ratios (ratio of ratios) of the red to infrared signals. This modulation ratio has been observed to correlate well to arterial oxygen saturation. The pulse oximeters and sensors are empirically calibrated by measuring the modulation ratio over a range of in vivo measured arterial oxygen saturations ($SaO_2$) on a set of patients, healthy volunteers, or animals. The observed correlation is used in an inverse manner to estimate blood oxygen saturation ($SpO_2$) based on the measured value of modulation ratios of a patient. The estimation of oxygen saturation using modulation ratios is described in U.S. Pat. No. 5,853,364, entitled "METHOD AND APPARATUS FOR ESTIMATING PHYSIOLOGICAL PARAMETERS USING MODEL-BASED ADAPTIVE FILTERING", issued Dec. 29, 1998, and U.S. Pat. No. 4,911,167, entitled "METHOD AND APPARATUS FOR DETECTING OPTICAL PULSES", issued Mar. 27, 1990, and the relationship between oxygen saturation and modulation ratio is further described in U.S. Pat. No. 5,645,059, entitled "MEDICAL SENSOR WITH MODULATED ENCODING SCHEME," issued Jul. 8, 1997, the disclosures of which are herein incorporated by reference in their entirety. Most pulse oximeters extract the plethysmographic signal having first determined saturation or pulse rate. An exemplary forehead oximetry sensor is described in a co-pending U.S. patent application Ser. No. 10/256,245, entitled: "Stacked Adhesive Optical Sensor," the disclosure of which is herein incorporated by reference in its entirety for all purposes.

The force applied to the oximetry sensor can be a factor in the proper functioning of the sensor. In certain clinical scenarios, a headband 200 is required to be used in conjunction with a forehead sensor 101 (e.g., an oximetry sensor), as is shown in FIG. 2. FIG. 2 shows the sensor leads extending from the sensor (not shown) outward from beneath the headband. Such clinical scenarios include scenarios where: patient is lying down with his/her head near or below chest level; patient is subject to elevated venous pressure; patient is diaphoretic; patient is moving excessively, such as during exercise; as well as other scenarios where venous pulsations can introduce errors in oximetry calculations. In those scenarios, without a headband, or force on the oximetry sensor, venous pulsations could cause an incorrect interpretation of the waveform, and therefore result in a less than accurate determination of the oxygen saturation and pulse rate values. The headband can be used to apply pressure to the oximetry sensor, thus reducing the effects of venous pulsations. When used to support an oximetry sensor, the amount of force applied by the sensor on the forehead should be greater than the venous pressure, but less than the arteriole pressure. Generally, a good pressure range is one where the applied pressure is higher than venous pressure (e.g., 3-5 mm Hg) and lower than the capillary pressure (e.g., 22 mm Hg). Preferably, this should be between 15 mm Hg and 20 mm Hg in the adult patient. The headband in accordance with the embodiments of the present invention may be adjusted for use with any size wearer by using an adjustable closure mechanism, such as for example a hook and loop closure mechanism. The user can apply a wide range of pressures to the forehead oximetry sensor depending on the amount of tension which has been applied to the headband during its placement around the wearer's head.

The embodiments of the present invention are intended to alleviate the guesswork by the caregivers by giving them a visual indicator of the proper amount of tension required in the headband during placement around the head. The required tension is related to the pressure being applied by the sensor when it is attached with the patient.

Figure 5:
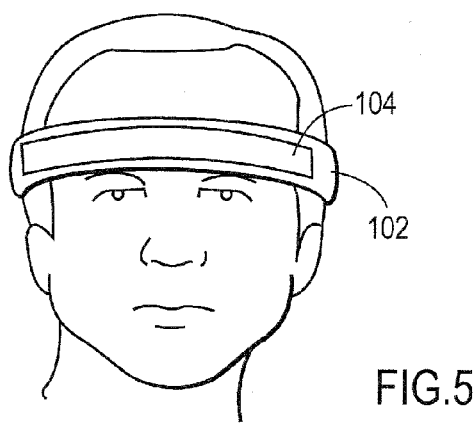
FIG. 5 is a front view diagram of an embodiment of the headband in accordance with the present invention shown worn by a user.
Figure 6:
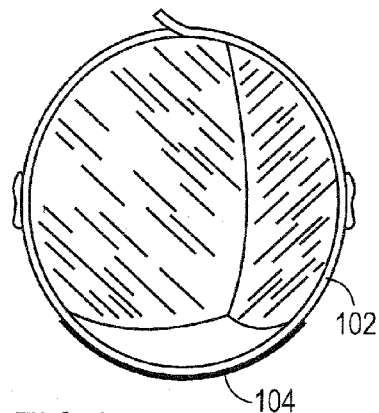
FIG. 6 is a top view diagram of an embodiment of the headband in accordance with the present invention shown in proper tension when worn by a user.
Figure 7:
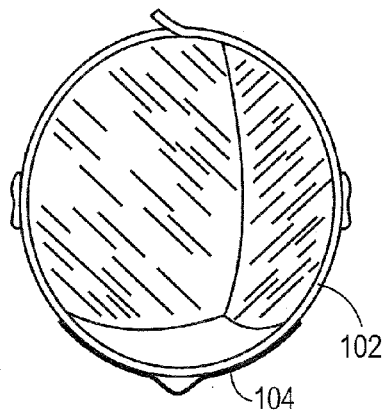
FIG. 7 is a top view diagram of an embodiment of the headband in accordance with the present invention shown in less than proper tension when worn by a user.

In one embodiment, shown in FIG. 3, an elastic headband 102 is shown in an unstretched position. A non-elastic fabric 104 is shown attached to the elastics portion 102 along two of its edges 106. The other two edges of the non-elastic portion are not attached to the elastic segment and are thus free to project outward away from the face of the elastic segment. The non-elastic segment is smaller the elastic segment. The non-elastic segment is sized to span a portion of the elastic segment when the elastic segment is stretched. The non-elastic segment is larger than the portion of the elastic segment it spans when the elastic segment is not stretched. As the elastic segment 102 is stretched from its non-stretched position, the non-elastic portion is pulled at its edges 106 along with the stretching elastic segment 102 until the elastic portion between the edges has stretched to a length equal to the length of the non-elastic portion. The headband also includes closure mechanisms (not shown), which are described below in conjunction with FIG. 4. FIG. 5 shows a front view diagram of an embodiment of the headband in accordance with the present invention shown worn by a user. It is noted that the headband may be used to hold and impart a pressure against a sensor, such as an oximetry sensor applied to a patient's forehead, as shown in FIG. 2. For clarity in describing the tension indicator, such a sensor is not shown in FIGS. 5-7. FIG. 6 is a top view diagram of an embodiment of the headband 102 in accordance with the present invention shown in proper tension when worn by a user. As is shown in this figure, when the headband is properly tightened, the pressure indicator portion 104 is pulled tight across the elastic portion 102, thus not providing a visual indication that the headband needs to be retightened. On the other hand, FIG. 7 shows a top view diagram of an embodiment of the headband in accordance with the present invention shown in less than proper tension when worn by a user. As is shown in FIG. 7, when a less than adequate pressure is being applied by the headband to a user's forehead, or when the headband is not tight enough, the indicator 104 projects out from the surface creating a loop which provides a visual cue that the headband needs re-tightening.

When the headband is not stretched there is an amount of slack between the non-elastic and elastic portions. When the headband is stretched, the slack in the non-elastic strap is eliminated, giving the visual indication that the headband stretch is sufficient. The headband is chosen to be long enough to fit around the head of a user (or patient). The elastic material may be made of any suitable fabric, such as an open cell urethane foam. The non-elastic strap, which is shorter than the elastic portion is sewn or attached otherwise (e.g., adhesively, etc.) onto the elastic headband at a spacing that is less than the lengths of the non-elastic portion. The non-elastic material may be made of any suitable fabric, such a Dacron-type fabric.

Figure 4:
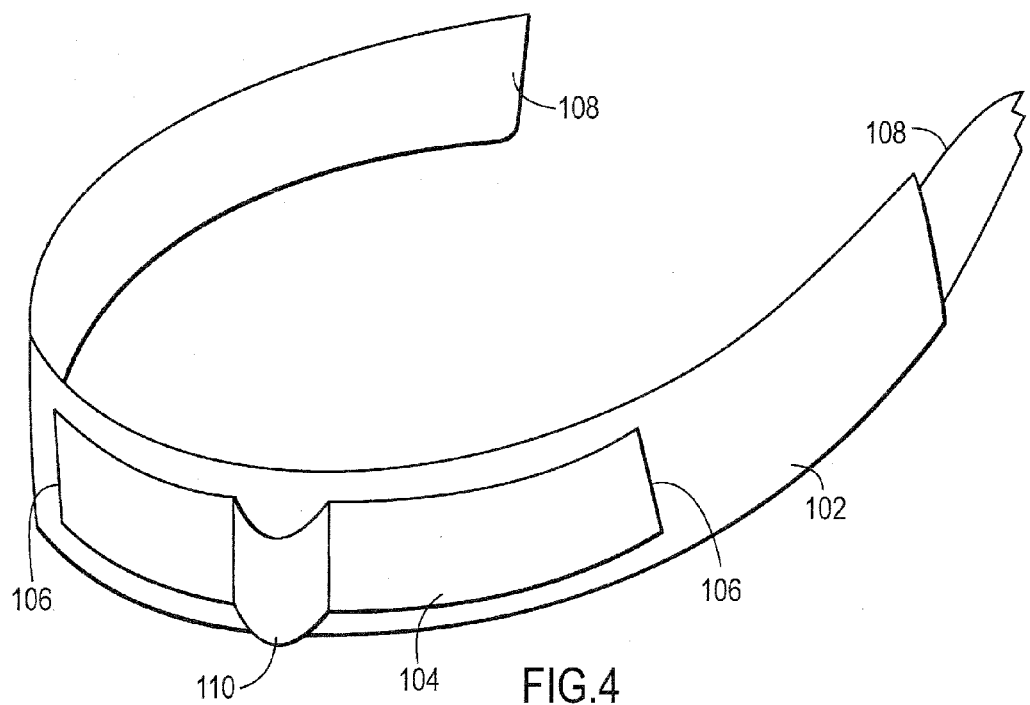
FIG. 4 is a diagram of an alternate embodiment of the headband in accordance with the present invention.

FIG. 4 is a diagram of an alternate embodiment of the headband in accordance with the present invention. An elastic headband 102 is shown in an unstretched position. A non-elastic fabric 104 is shown attached to the elastics portion 102 along two of its edges 106. The other two edges of the non-elastic portion are not attached to the elastic segment and are thus free to project outward away from the face of the elastic segment. The non-elastic segment 104 is smaller the elastic segment 102. The non-elastic segment is sized to span a portion of the elastic segment when the elastic segment is stretched. The non-elastic segment is larger than the portion of the elastic segment it spans when the elastic segment is not stretched. As the elastic segment 102 is stretched from its non-stretched position, the non-elastic portion is pulled at its edges 106 along with the stretching elastic segment 102 until the elastic portion between the edges has stretched to a length equal to the length of the non-elastic portion.

FIG. 4 also shows the non-elastic portion to include a permanent crease or a fold 110. As shown in FIG. 4A, such a fold 110 may be made by overlapping the non-elastic portion to form a fold and then heat pressing or heat sealing the fabric to form a permanent fold or crease. In one embodiment, the fold or crease is made in the middle of the inelastic segment, which causes it to project outward in a sharp, angular fashion as the elastic band 102 retracts or relaxes. In operation, it has been shown that the sharp, angular crease or fold acts as a mechanical amplifier and provides a more distinct visual cue and better sensitivity as to when the threshold of minimal headband tension has been passed. The creased tension indicator 110 exhibits increased sensitivity to a loss in headband tension by projecting further away from the elastic band in a skewed fashion. The creased tension indicator 110 provides a more pronounced visual cue both from the perspective of looking directly at the forehead and from looking down at the top (edge) of the headband. The material chosen for the inelastic portion having a fold or a crease can be similar to the noncreased or non-folded inelastic material. In addition, a material such a polyester webbing material, which is capable of holding a fold or a crease, may also be used. The elastic material may be made of a material as is described above, or made using other suitable material such as a terry band.

When the headband is not stretched there is an amount of slack between the non-elastic and elastic portions. When the headband is stretched, the slack in the non-elastic strap is eliminated, giving the visual indication that the headband stretch is sufficient.

Also shown in FIG. 4, and applicable to the embodiment described in conjunction with FIG. 3, is the closure device 108. One such closure device is a hook and loop type closure. The headband in accordance with the embodiments of the present invention may use other closure mechanisms such as snaps, buttons, adhesives, pins, or combinations thereof, as well as others known to those of skill in the relevant arts. Alternately, the headband may be a pre-formed loop, without a separate closure mechanism.

The headband described above includes a sensor attachment pressure indicator. As described above, the headband may be used to allow a sensor's attachment pressure with the patient's tissue location (e.g. forehead, and so on) to be chosen which is greater than venous pulsations (e.g., 5-10 mm Hg) but less than a maximum amount (e.g., 30 mm Hg, or so). As described above, such a pressure indicator is attached with the headband. Alternately, the pressure indicator may be attached with the sensor, such as an oximetry sensor. One embodiment of the pressure indicator is a tension indicator as described above with reference to FIGS. 3-4. Other pressure indicating means include pressure or force sensors small and light enough to be included with either the sensor or the headband assembly.

The information provided by the pressure indicator may be used to help establish an acceptable windows of pressure for the sensor's attachment with a patient. The acceptable window of pressure may also be enhanced to include the affects of the patient's head elevation relative to the patient's heart.

Additionally, the concept of using a headband to ensure an acceptable sensor attachment pressure is extendible to other patient body locations; locations where a sensor attachment pressure can help provide a more accurate sensor reading.

Figure 8:
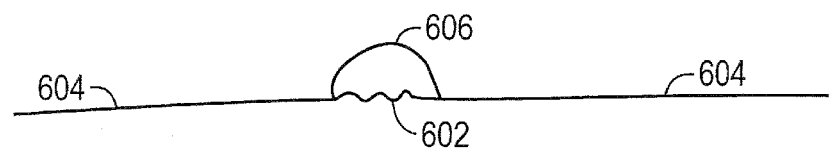
FIG. 8 is a diagram of an alternate embodiment of the headband in accordance with the present invention.

An alternate embodiment of the tension or pressure indicating headband in accordance with the present invention is shown in FIG. 8. As is shown in FIG. 8, the headband includes an inelastic portion 604 and an elastic portion 602. The tension indicating portion 606 is also made of an inelastic material. The tension indicating portion 606 may be a creased or folded as described in conjunction with FIG. 4 or as is shown uncreased or unfolded as described in conjunction with FIG. 3. The description of the closure devices and how the elastic and inelastic portions are attached to one another are also set forth above. In this embodiment, the main stretchable portion is elastic portion 602. Once the headband has been stretched such that section 602 is stretched to match the length of section 606, the headband's stretch will be limited. This embodiment by having a shorter elastic portion limits the extension of the headband and hence limits the range of pressures that can be applied by the headband against a user's forehead or the sensor applied to a user's forehead.

As will be understood by those skilled in the art, the present invention may be embodied in other specific forms without departing from the essential characteristics thereof. These other embodiments are intended to be included within the scope of the present invention, which is set forth in the following claims.

What is claimed is:

1. A headband, comprising:
    an elastic segment sized to fit around a wearer's head;
    a non-elastic segment being smaller than and attached to the elastic segment on an exterior side of the elastic segment, wherein the exterior side of the elastic segment generally faces away from the wearer when the headband is applied to the wearer's head, and the non-elastic segment is sized to span a portion of the elastic segment when the elastic segment is stretched, the non-elastic segment being larger than the portion of the elastic segment it spans when the elastic segment is not stretched; and
    a sensor coupled to the headband on a patient side of the elastic segment opposite the exterior side.

2. The headband of claim 1 comprising a closure mechanism coupled with the elastic portion.

3. The headband of claim 2 wherein the closure mechanism is a hook and loop closure, a snap, a button, an adhesive, a pin, or combinations thereof.

4. The headband of claim 1 wherein the elastic segment is rectangular shaped having a long and a short dimension, and the non-elastic segment is attached along a set of its edges with the elastic segment, wherein the set of edges are generally parallel to the short dimension.

5. The headband of claim 1 wherein the non-elastic segment is attached with the elastic segment in such a manner that the non-elastic segment projects out from the exterior surface of the elastic portion when the headband is not sufficiently tight, thus creating a loop which provides a visual indication that the headband needs re-tightening.

6. The headband of claim 1 wherein the non-elastic segment is formed with a fold or a crease, which causes the non-elastic portion to project out from the exterior surface of the elastic portion in a pronounced fashion as the elastic segment retracts.

7. The headband of claim 5 wherein the non-elastic segment is sized to not project out from the exterior surface of the elastic portion when the headband is sufficiently tight thus indicating an adequate level of tension corresponding with delivering a pressure in a range higher than venous pressure and lower than capillary pressure to the forehead of the wearer.

8. A headband, comprising:
    an inelastic segment sized to fit around a wearer's head; and
    an elastic segment being smaller than and attached to the inelastic segment such that the elastic segment is visible to an observer when the headband is applied to the wearer's head, the elastic segment sized to span a portion of the inelastic segment when elastic segment is stretched, the elastic segment being smaller than the portion of the inelastic segment it spans when the elastic segment is not stretched; and
    a sensor coupled to the headband on a patient side of the inelastic segment opposite the exterior side.

9. The headband of claim 8 comprising a closure mechanism coupled with the elastic portion.

10. The headband of claim 9 wherein the closure mechanism is a hook and loop closure, a snap, a button, an adhesive, a pin, or combinations thereof.

11. The headband of claim 8 wherein the inelastic segment is rectangular shaped having a long and a short dimension, and the elastic segment is attached along a set of its edges with the inelastic segment, wherein the set of edges are generally parallel to the short dimension.

12. The headband of claim 8 wherein the elastic segment is attached with the inelastic segment in such a manner that the non-elastic segment projects out from the surface adjacent to a user's forehead when the headband is not sufficiently tight, thus creating a loop which provides a visual indication that the headband needs re-tightening.

13. The headband of claim 12 wherein the non-elastic segment is sized to not project out from the surface when the headband is sufficiently tight thus indicating an adequate level of tension corresponding with delivering a pressure in a range higher than venous pressure and lower than capillary pressure to the wearer's forehead.

14. A headband, comprising:
    an elastic segment sized to fit around a wearer's head; and
    a non-elastic segment smaller than and attached discontinuously to an exterior side of the elastic segment, such that the nonelastic segment has some slack when the elastic segment is in an unstretched state, wherein the exterior side of the elastic segment generally faces away from the wearer when the headband is applied to the wearer's head, and the nonelastic segment has less slack when the elastic segment is applied to the patient's head with sufficient tension to deliver pressure in the range higher than venous pressure and lower than capillary pressure to the wearer's head.

15. The headband of claim 14 comprising a closure mechanism coupled with the elastic portion.

16. The headband of claim 15 wherein the closure mechanism is a hook and loop closure, a snap, a button, an adhesive, a pin, or combinations thereof.

17. The headband of claim 14 wherein the non-elastic segment is attached with the elastic segment in such a manner that the non-elastic segment projects out from the surface of the elastic portion when the headband is not sufficiently tight, thus creating a loop which provides a visual indication that the headband needs re-tightening.

18. The headband of claim 14 wherein the non-elastic segment is sized to have no slack when the headband is applied with sufficient tension to deliver pressure in the range higher than venous pressure and lower than capillary pressure to the wearer's head.

19. The headband of claim 14, wherein the headband is coupled to a sensor.

20. The headband of claim 1 wherein the sensor is a pulse oximetry sensor.

21. The headband of claim 8 wherein the sensor is a pulse oximetry sensor.

22. The headband of claim 1 wherein the sensor is removably coupled to the headband by the tension of the headband after the headband has been applied to the to the wearer's forehead.

23. A headband, comprising:
    an elastic segment sized to fit around a wearer's head; and
    a non-elastic segment smaller than and attached discontinuously to an exterior side of the elastic segment such that the non-elastic segment is visible to an observer when the headband is applied to the wearer's head, wherein the non-elastic segment is attached with the elastic segment in such a manner that the non-elastic segment projects out from the surface of the elastic portion when the headband is not sufficiently tight, thus creating a loop which provides a visual indication to the observer that the headband needs re-tightening.

* * * * *